United States Patent [19]

Bullock

[11] 4,181,741
[45] Jan. 1, 1980

[54] NAPHTHALENE MITICIDES

[75] Inventor: Greg A. Bullock, Hockessin, Del.

[73] Assignee: E. I. Du Pont de Nemours and Company, Wilmington, Del.

[21] Appl. No.: 852,762

[22] Filed: Nov. 18, 1977

[51] Int. Cl.$^2$ .................. A01N 9/24; C07C 69/02; C07C 69/18; C07C 69/96
[52] U.S. Cl. .................... 424/311; 424/301; 560/139; 260/463
[58] Field of Search ............... 560/139; 424/311, 301; 260/463

[56] References Cited

U.S. PATENT DOCUMENTS

| | | | |
|---|---|---|---|
| 4,053,634 | 10/1977 | Bellina et al. | 424/311 |
| 4,055,661 | 10/1977 | Bellina et al. | 424/311 |

OTHER PUBLICATIONS

Fieser et al., JACS 70, pp. 3156–3164 (1948).
Fieser et al., JACS 70, pp. 71–75 (1948).
Fieser, JACS 70, pp. 3165–3174 (1948).

*Primary Examiner*—Jane S. Myers

[57] ABSTRACT

Compounds of the formula

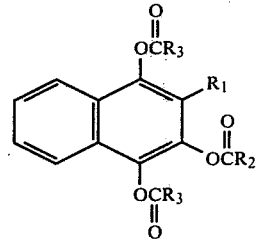

wherein
$R_1$ is straight chain alkyl of 11–14 carbon atoms; and
$R_2$ and $R_3$ are independently alkyl of 1–6 carbon atoms or alkoxy of 1–4 carbon atoms
are effective in eradicating mites.

5 Claims, No Drawings

NAPHTHALENE MITICIDES

BACKGROUND OF THE INVENTION

This invention relates to the use of naphthalenetriol esters in agricultural applications for controlling mites.

U.S. Pat. Nos. 4,053,634 and 4,055,661 disclose the use of 2-higher alkyl-3-hydroxy-1,4-naphthoquinone carboxylic acid esters for controlling mites and aphids which are detrimental to plants.

Fieser, "Diene Synthesis of 1,4-Naphthoquinones", J.A.C.S., 70, 3165–3175 (1948) discloses improved procedures for preparing α-naphthoquinone and for converting it into various naphthalene derivatives such as 1,2,4-triacetoxynaphthalene.

Neither reference suggests that naphthalenetriol esters would be effective against mites when applied topically to plants.

SUMMARY OF THE INVENTION

Naphthalenetriol derivatives of the formula

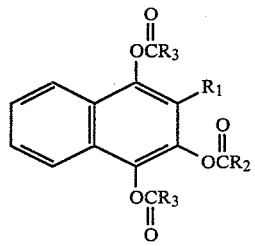

(I)

wherein
$R_1$ is straight chain alkyl of 11–14 carbon atoms; and
$R_2$ and $R_3$ are independently alkyl of 1–6 carbon atoms or alkoxy of 1–4 carbon atoms are effective in eradicating mites. These compounds are useful for protecting plants from damage caused by mites when applied topically to the plants using known techniques.

This invention also includes miticidal compositions and mixtures which contain at least one compound of formula I as active ingredient.

Preferred for their ease of synthesis and/or more favorable cost and/or higher miticidal activity, are those compounds of formula I wherein $R_2$ and $R_3$ are independently alkyl of 1—3 carbon atoms or alkoxy of 1-2 carbon atoms.

More preferred for their greater biological activity and/or favorable cost are those compounds of formula I wherein $R_2$ and $R_3$ are independently alkyl of 1-3 carbon atoms. Specifically, the following compounds are preferred for their highest miticidal activity and for economical reasons:

1,2,4-naphthalenetriol-3-dodecyl triacetate; (m.p. 97°–99° C.)

1,2,4-naphthalenetriol-3-dodecyl tripropionate, (m.p. 52°–55° C.)

DESCRIPTION OF THE INVENTION

Synthesis

The compounds of formula I may be prepared from 3-acyloxy-2-alkyl-1,4-naphthoquinones which are described in U.S. Pat. No. 4,053,634 and 4,055,661, the teachings of which are incorporated herein by reference. The 3-acyloxy-2-alkyl-1,4-naphthoquinones are heated with an excess of the appropriate acid anhydride and a reducing agent such as zinc dust in the presence of a catalytic amount of a nonprotic base such as triethyl amine. The reaction products are isolated by filtering the warm reaction mixture to remove any insoluble salts and then quenching the filtrate with cold water. The compounds of this invention are isolated by methods well known in the art, e.g., extraction. The following examples illustrate the above-described processes.

EXAMPLE 1

Preparation of 1,2,4-naphthalenetriol-3-docecyl triacetate

A suspension of 20 grams (0.052 mole) of 3-acetyloxy-2-dodecyl-1,4-naphthoquinone in 50 ml. of acetic anhydride is warmed to 35°–40° C.; 4.1 grams (0.062 mole) of zinc dust is added to the suspension followed by the addition of 0.5 ml of triethylamine. The reaction mixture is stirred vigorously and warmed to about 45°–50° C. At this temperature a strong exotherm sets in and heating is discontinued as the temperature rises to about 120° C. When the temperature of the reaction mixture has cooled to about 80° C., heat is reapplied, and the mixture is stirred at the 80° C. temperature for 3.5 hours and then filtered hot. The warm filtrate is poured into ice water with stirring. The solid product is filtered, washed with distilled water, and recrystallized from methanol, affording 20 grams of white powder, m.p. 97°–99° C.

EXAMPLE 2

Preparation of 1,2,4-naphthalenetriol-3-dodecyl tripropionate

A suspension of 2 grams (0.0052 mole) 3-acetyloxy-2-dodecyl-1,4-naphthoquinone in 5 ml propionic anhydride is warmed to about 35°–40° C. and 0.41 grams (0.0052 mole) of zinc dust is added followed by the addition of 2 drops triethylamine. The reaction mixture is heated at about 90°–100° C. for 2.5 hours with vigorous stirring. The hot reaction mixture is then filtered, and poured into ice water. The solid product is filtered off, washed with distilled water, and recrystallized from methanol affording 1.9 grams of white powder, m.p. 52°–55° C.

By using the appropriate 3-acyloxy-2-alkyl-1,4-naphthoquinone and the appropriate acid anhydride, the following compounds shown in Table 1 could be similarly prepared by anyone skilled in the art, using the procedure outlined in Examples 1 and 2.

TABLE 1

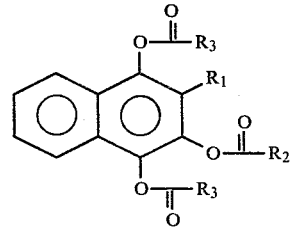

| $R_1$ | $R_2$ and $R_3$ |
| --- | --- |
| n-undecyl | 2-methylpropyl |
| n-dodecyl | propyl |
| n-tridecyl | butyl |
| n-dodecyl | 1-methylethyl |
| n-tetradecyl | 1-methylethyl |
| n-dodecyl | pentyl |
| n-dodecyl | methyl |

TABLE 1-continued

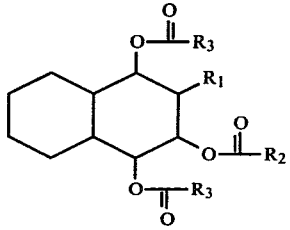

| R₁ | R₂ and R₃ |
|---|---|
| n-dodecyl | methoxy |
| n-undecyl | ethoxy |
| n-tridecyl | propoxy |
| n-dodecyl | hexyl |
| n-dodecyl | 2-methylpropoxy |

Formulation and Use

The compounds of Formula I are useful as miticides for the protection of a wide variety of plants from damage caused by these pests. More specifically, fruits, field crops, vegetables, and ornamentals can be protected.

When mites come into contact with the compounds of this invention, either in the form of direct sprays or by walking over surfaces which have been treated therewith, they rapidly become irritated and leave the area or are killed if they have been exposed to a sufficiently high dosage. While most plants or animals can tolerate small numbers of mites without apparent adverse effect, mite populations can grow rapidly and easily outstrip parasite and predator capabilities for control. Growers noting rapid mite build-up must take immediate action to prevent damage to economically important crops. Thus, biologically effective compounds are needed which immediately reduce mite build-up and thereby prevent damage to important crops.

The method of this invention, namely, contacting mites with a miticidally effective concentration of the compounds of Formula I, is a most desirable method for controlling these pests. For instance, very small quantities of compounds of Formula I are required for miticidal activity; additionally, the compounds are not rapidly washed from leaves by rain.

The quantity of compound needed for mite control will vary depending on the specific situation. Among the variables that must be considered in determining the quantity of chemical to be used are the specific compound itself, the specific mite to be controlled, weather conditions, the type of crop, the stage of development of the crop, the volume of spray applied, population pressure, and the interval between applications. For plant protection, solutions or suspensions containing as little as 20 ppm of active ingredient in a spray solution can be effective under a given set of circumstances. For field usage, however, in high-volume applications, aqueous spray preparations containing 150–15,000 ppm of active ingredient are generally useful. Preferred are suspensions containing 350–4,000 ppm. and most preferred are preparations containing 600–2,000 ppm. On an area basis, in general, 0.15 to 60 kilograms of active ingredient per hectare are acceptable, preferably 0.25 to 30 kilograms, and most preferably 0.5 to 15 kg. When applied in an orchard, spraying is continued until run-off is observed.

It may be desirable or useful to mix the compounds of this invention with other agricultural pesticides or adjuvants. Such mixtures often increase the effectiveness of the application on mites and broaden the scope of control to embrace other pests such as insects, fungi, nematodes, or bacteria. Other pesticides with which the compounds of this invention may be mixed to achieve increased activity include

| | |
|---|---|
| diazinon | O,O-diethyl O-(2-isopropyl-4-methyl-6-pyrimidyl)phosphorothioate |
| disulfoton | O,O-diethyl S-2-(ethylthio)ethyl-phosphorodithioate |
| phorate | O,O-diethyl S-(ethylthio)methyl-phosphorodithioate |
| omite ® | 2(p-tert-butylphenoxy)cyclohexyl 2-propynyl sulfite |
| chlordimeform | N'-(4-chloro-2-methyl phenyl) N,N-dimethylmethaninimide |
| oxamyl | S-methyl 1-(dimethylcarbamoyl)-N-[(methylcarbamoyl)oxy]thioformimidate |
| methomyl | S-methyl N-(methylcarbamoyloxy)-thioacetimidate |
| benomyl | 1-butylcarbamoyl-2-benzimidazole-carbamic acid, methyl ester |
| captan | N-(trichloromethylthio)-3a,4,7,7a-tetrahydrophthalimide |
| maneb | ethylenebisdithiocarbamic acid, manganese salt |
| BAAM ® | Methanimidamide, NPR-/2,4-dimethyl-phenyl/-N-// /2,4-dimethylphenyl-imino/methyl//-N-methyl |
| PP-199 | benzenamine N-//2-chloro-5-/trifluoromethyl/phenyl//-2,4-dinitro-6-/trifluoromethyl/- |
| Kelthane ® | Ethanol 1,1-bis(p-chlorophenyl)-2,2,2-trichloro- |
| Trithion ® | Phosphorodithioic acid S-(p-chloro-phenylthiomethyl) O,O-diethyl ester |
| Vendex ® | Distannoxane 1,1,1,3,3,3-hexakis/2-methyl-2-phenylpropyl/- |
| Morestan ® | 1,3-dithiolo//2,3-B//quinoxolin-2-one, 6-methyl- |
| Morocide | Senecioic acid, ester with phenol, 2-sec-butyl-4,6-dinitro- |
| Plictran | Tin tricyclohexylhydroxy- |
| Zardex | Cyclopropanecarboxylic acid hexadecyl ester |
| Carzol | N'-(3-hydroxyphenyl)-N,N-dimethyl-methanimidamide, methyl carbamate 3-acetyloxy-2-n-dodecyl-1,4-naphthoquinone |
| carboxin | 5,6-dihydro-2-methyl-1,4-oxathiin-3-carboxanilide |
| streptomycin | 2,4-diguanidino-3,5,6-trihydroxy-cyclohexyl-5-deoxy-2-o-(2-deoxy-2-methylamino-α-glycopyranosyl)-3-formylpentofuranoside |

In an embodiment of the instant invention, compounds of Formula I are admixed with 3-acetoxy-2-n-dodecyl-1,4-naphthoquinone in the ratio of 1:10 to 10:1 for improved knockdown and residual control of mites.

The compounds of this invention are especially suited for the protection of living plants such as fruit-bearing trees, nut-bearing trees, ornamental trees, forest trees, vegetable crops, horticultural crops (including ornamentals, small fruit and berries) and grain and seed crops. Apple trees, peach trees, cotton, citrus trees, beans and peanuts are particularly susceptible to mite damage and can be protected by application of the compounds of this invention. To assure control throughout the growing season (e.g., June through August in the Northern Hemisphere) multiple applications at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two spotted mite) which are commonly called "orchard mites", and which attack a great many deciduous trees, such as apple, pear, cherry, plum and peach trees; *Tetranychus atlanticus* (Atlantic or strawberry mite), *T. cinnabarinus* (carmine spider mite) and *T. pacificus* (Pacific mite); which attack cotton and numerous other crop plants; *Paratetranychus citri* (citrus red mite) and others which attach citrus; *Phyllocoptruta oleivora* which causes citrus rust; *Bryobia praetiosa* (clover mite) which attacks clover, alfalfa and other crops; and *Aceria neocynodomis* which attacks grasses and other plants.

Useful formulations of the compounds of formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight | | |
| --- | --- | --- | --- |
|  | Active Ingredient(s) | Diluent(s) | Surfactant(s) |
| Wettable Powders | 20–60 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactants to active ingredient are sometimes desirable, and are achieved by incorporation into the formulation or by tank mixing.

Typical solid diluents are described in Watkins, et al., "Handbook of Insecticide Dust Diluents and Carriers", 2nd. Edn., Dorland Books, Caldwell, N.J. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff, and "Perry's Chemical Engineer's Handbook", 4th. Edn., McGraw-Hill, N.Y., 1963, pp. 8–59ff.

For further information regarding the art of the formulation, see for example:

- J. B. Buchanan, U.S. Pat. No. 3,576,834, Apr. 27, 1971, Col. 5, line 36 through Col. 7, line 70, and Ex. 1–4, 17, 106, 123–140.
- R. R. Shaffer, U.S. Pat. No. 3,560,616, Feb. 2, 1971, Col. 3, line 48 through Col. 7, line 26 and Examples 3–9, 11–18.
- E. Somers, "Formulation", Chapter 6 in "Fungicides", Vol. I, Academic Press, New York, 1967.

Typical formulations, i.e., compositions, containing the compounds of this invention are illustrated in the following examples.

EXAMPLE 3

| Wettable Powder | |
| --- | --- |
| 1,2,4-naphthalenetriol-3-dodecyl triacetate | 20% |
| 3-acetyloxy-2-n-dodecyl-1,4-naphthoquinone | 20% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended and passed through an air mill to produce an average particle size under 15 microns, reblended, and sifted through a U.S.S. No. 50 sieve (0.3 mm opening) before packaging.

All compounds of the invention may be formulated in the same manner.

EXAMPLE 4

| Wettable Powder | |
| --- | --- |
| 1,2,4-naphthalenetriol-3-dodecyl tripropionate | 25% |
| 3-acetyloxy-2-n-dodecyl-1,4-naphthoquinone | 25% |
| sodium alkylnaphthalenesulfonate | 2% |
| low viscosity methyl cellulose | 2% |
| diatomateous earth | 46% |

The ingredients are blended, coarsely hammer-milled and then airmilled to produce particles of active essentially all below 10 microns in diameter. The product is reblended before packaging.

EXAMPLE 5

| Emulsifiable Concentrate | |
| --- | --- |
| 1,2,4-naphthalenetriol-3-dodecyl triacetate | 15% |
| 3-acetyloxy-2-n-dodecyl-1,4-naphthoquinone | 15% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 6

| Emulsifiable Concentrate | |
|---|---|
| 1,2,4-naphthalenetriol-3-dodecyl triacetate | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 7

| Wettable Powder | |
|---|---|
| 1,2,4-naphthalenetriol-3-docecyl triacetate | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended and passed through an air mill to produce an average particle size under 15 microns, reblended, and sifted through a U.S.S. No. 50 sieve (0.3 mm opening) before packaging.

All compounds of the invention may be formulated in the same manner.

EXAMPLE 8

| Wettable Powder | |
|---|---|
| 1,2,4-naphthalenetriol-3-dodecyl tripropionate | 50% |
| sodium alkylnaphthalenesulfonate | 2% |
| low viscosity methyl cellulose | 2% |
| diatomateous earth | 46% |

EXAMPLE 9

| | |
|---|---|
| 1,2,4-naphthalenetriol-3-dodecyl tripropionate | 5% |
| attapulgite | 15% |
| talc | 80% |

The active ingredient is blended with attapulgite and then passed through a hammer mill to produce particles substantially all below 200 microns. The ground concentrate is then blended with powdered talc until homogeneous.

EXAMPLE 10

Test units consisted of plant pots containing two red kidney bean plants in the two-leaf stage per pot. The plants were infested with two-spotted mites and sprayed to run-off with 50 ppm solutions of compounds of this invention. Solutions were made by dissolving weighed quantities of the active ingredients in 10 ml of acetone and then diluting to volume with water containing 1:3,000 of a surfactant, Duponol*L 144 WDG. Mite mortality was evaluated two days after spraying. The results are shown below.
*DuPonol L 144 WDG is a trade name of E. I. du Pont deNemours and Company for sodium alcohol sulfate.

COMPOUNDS

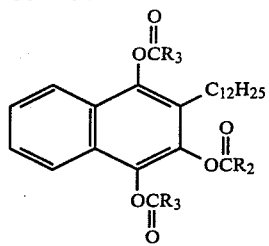

| $R_2$ and $R_3$ | Percent Mite Mortality 2 days |
|---|---|
| $CH\begin{array}{c}CH_3\\CH_3\end{array}$ | 95 |
| $CH_2CH_2CH_3$ | 97 |
| Untreated Control | 5 |

EXAMPLE 11

Bean plants infested with 2-spotted mites were sprayed to run-off with a 20 ppm solution of 1,2,4-naphthalenetriol-3-dodecyl tripropionate in Duponol L 144 WDG:$H_2O$ at 1:3000. Mite mortality was evaluated after two days.

| Spray Concentration (ppm) | Percent Mortality in 2 days |
|---|---|
| 20 | 96 |
| Untreated Control | 5 |

EXAMPLE 12

Bean plants infested with 2-spotted mites were sprayed with two compounds:
I. 1,2,4-naphthalenetriol-3-dodecyltriacetate
II. 3-acetyloxy-2-n-dodecyl-1,4-naphthoquinone These were prepared in Duponol L 144 WDG:$H_2O$ at 1:3000, and applied to the plants individually and in combination. In 14 days, the mixture of I and II significantly improved the level of control provided by either compound individually, as indicated by mite feeding injury. The results are shown below.

| Compound | Spray Concentration (ppm) | 14th day Feeding Injury* |
|---|---|---|
| I | 50 | 8 |
| II | 10 | 4 |
| I and II | 5 and 5 | 1 |
| Untreated Control | — | 7 |

*Feeding Injury Rating
0 = no injury
10 = plant completely destroyed.

EXAMPLE 13

Bean plants are infested with 2-spotted mites, were sprayed to run-off with a solution of 1,2,4-naphthalenetriol-3-dodecyltriacetate, prepared in Duponal L 144 WDG:$H_2O$ at 1:3,000. Mite mortality was evaluated after 2 days.

| Spray Concentration (ppm) | Percent Mortality in 2 Days |
| --- | --- |
| 50 | 78 |
| 100 | 71 |
| Untreated Control | 0 |

What is claimed is:

1. A method for protecting plants from mites comprising applying to the plant locus to be protected an effective amount of a compound of the formula:

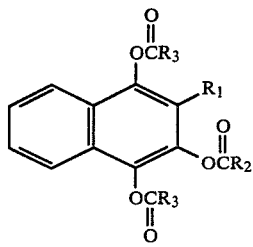

wherein $R_1$ is straight chain alkyl of 11–14 carbon atoms; and
$R_2$ and $R_3$ are independently alkyl of 1–6 carbon atoms or alkoxy of 1–4 carbon atoms.

2. A method for protecting plants from mites comprising applying to the plant locus to be protected an effective amount of the compound of claim 1 wherein $R_2$ and $R_3$ are independently alkyl of 1–3 carbon atoms or alkoxy of 1–2 carbon atoms.

3. A method for protecting plants from mites comprising applying to the plant locus to be protected an effective amount of the compound of claim 2 wherein $R_2$ and $R_3$ are independently alkyl of 1–3 carbon atoms.

4. A method for protecting plants from mites comprising applying to the plant locus to be protected an effective amount of the compound of claim 3 which is 1,2,4-naphthalenetriol-3-dodecyl triacetate.

5. A method for protecting plants from mites comprising applying to the plant locus to be protected an effective amount of the compound of claim 3 which is 1,2,4-naphthalenetriol-3-dodecyl tripropionate.

* * * * *